(12) United States Patent
Duffner

(10) Patent No.: US 6,796,986 B2
(45) Date of Patent: Sep. 28, 2004

(54) ADJUSTABLE TIBIAL OSTEOTOMY JIG AND METHOD

(76) Inventor: David W. Duffner, P.O. Box 342737, Austin, TX (US) 78734

( * ) Notice: Subject to any disclaimer, the term of this patent is extended or adjusted under 35 U.S.C. 154(b) by 140 days.

(21) Appl. No.: 10/107,563

(22) Filed: Mar. 26, 2002

(65) Prior Publication Data

US 2002/0165552 A1 Nov. 7, 2002

Related U.S. Application Data

(60) Provisional application No. 60/279,220, filed on Mar. 29, 2001.

(51) Int. Cl.$^7$ .............................................. A61B 17/56
(52) U.S. Cl. ......................................... 606/87; 606/86
(58) Field of Search .............................. 606/87, 88, 89, 606/90, 98, 96, 102, 97, 79, 82, 207, 208; 623/20.15, 20.16

(56) References Cited

U.S. PATENT DOCUMENTS

| | | | | |
|---|---|---|---|---|
| 4,421,112 A | | 12/1983 | Maines et al. ................ | 128/92 |
| 4,750,481 A | | 6/1988 | Reese .......................... | 128/92 |
| 5,053,039 A | * | 10/1991 | Hofmann et al. ............. | 606/87 |
| 5,275,603 A | | 1/1994 | Ferrante et al. ............... | 606/86 |
| 5,297,538 A | * | 3/1994 | Daniel ......................... | 600/206 |
| 5,306,276 A | | 4/1994 | Johnson et al. ............... | 606/86 |
| 5,445,640 A | | 8/1995 | Johnson et al. ............... | 606/86 |
| 5,451,228 A | | 9/1995 | Johnson et al. ............... | 606/86 |
| 5,540,695 A | * | 7/1996 | Levy ........................... | 606/87 |
| 5,601,565 A | | 2/1997 | Huebner ...................... | 606/87 |
| 5,613,969 A | * | 3/1997 | Jenkins, Jr. ................... | 606/87 |
| 5,681,316 A | | 10/1997 | DeOrio et al. ................ | 606/88 |
| 5,722,978 A | * | 3/1998 | Jenkins, Jr. ................... | 606/87 |
| 5,911,724 A | | 6/1999 | Wehrli ......................... | 606/88 |
| 5,980,526 A | * | 11/1999 | Johnson et al. ............... | 606/86 |
| 6,027,504 A | | 2/2000 | McGuire ...................... | 606/87 |

* cited by examiner

*Primary Examiner*—Pedro Philogene
(74) *Attorney, Agent, or Firm*—John A. Thomas

(57) ABSTRACT

An adjustable tibial osteotomy jig, comprises a goniometer, and the goniometer further comprises first an second arms, each arm having a base. A pivot movably connects the arms at the bases. The pivot has a bore passing through it. A proximal and distal cutting guide are mounted on the first and second arms, respectively. The cutting guides each have a slot to receive a saw blade. Each cutting guide is clamped in a predetermined position along its respective arm. One or more pins pass through the holes in the proximal cutting guide and into a tibia, for fixing the proximal cutting guide in a first predetermined position with respect to the tibia. One or more pins pass through the holes in the distal cutting guide for fixing the distal cutting guide in a second predetermined position with respect to the tibia The surgeon passes the blade of a saw through the slots of the cutting guides, which results in a cut removing a wedge-shaped piece of bone from the tibia.

8 Claims, 6 Drawing Sheets

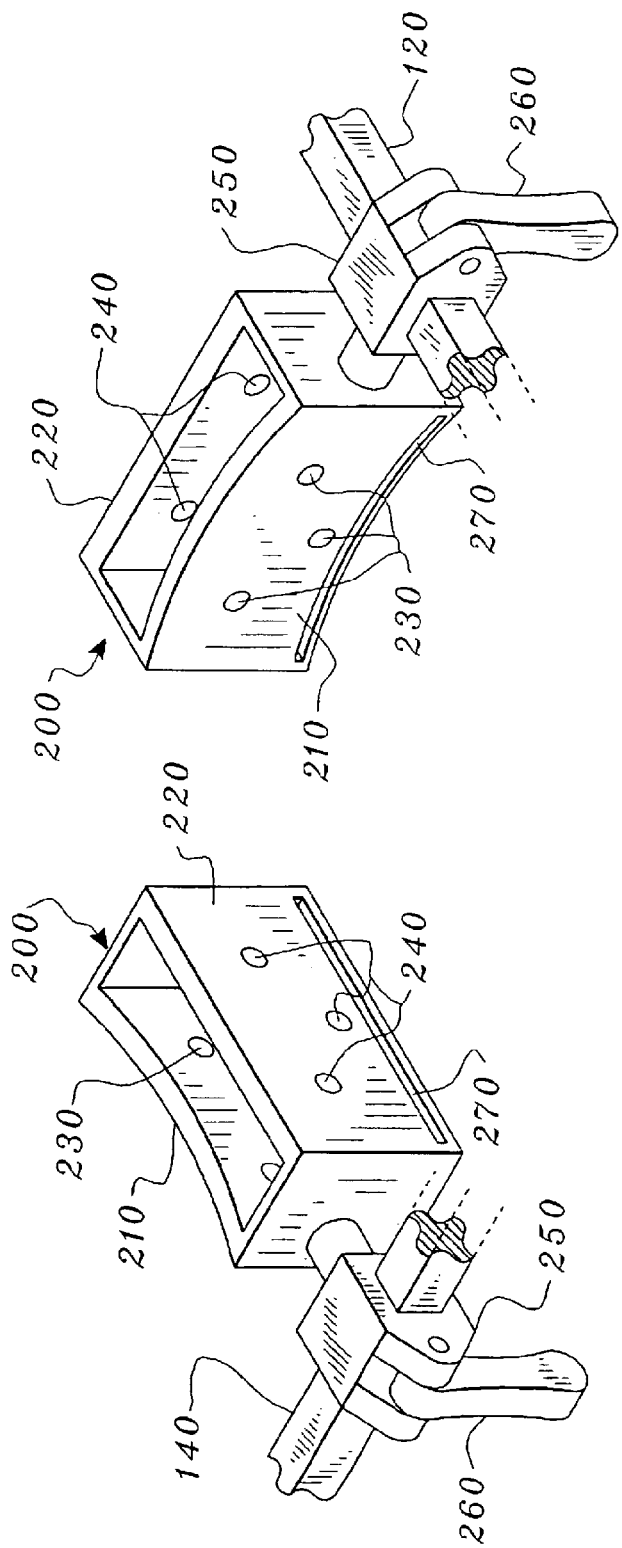
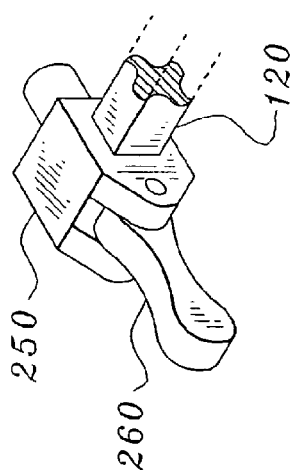
Fig. 2
Fig. 3
Fig. 4

ADJUSTABLE TIBIAL OSTEOTOMY JIG AND METHOD

CLAIM FOR PRIORITY

This application claims the priority of U.S. Provisional Application, Ser. No. 60/279,220, filed Mar. 29, 2001.

FIELD OF THE INVENTION

The present invention relates to devices and methods used to perform cuneiform, or wedge, osteotomy procedures on long bones, particularly in the upper tibial region.

BACKGROUND OF INVENTION

The articulation of the tibia and femur of a normal human knee joint is not perfectly straight, but is bent outward or away from the centerline of the body. This condition is known as valgus, with the normal considered to be at approximately six degrees. This creates a mechanical axis extending from the head of the femur, through the center of the knee joint, to the center of the ankle joint. Assuming the mechanical axis of the leg is within normal parameters, the loading patterns on the leg, which can be great, will be properly distributed.

Several conditions can lead to an alteration of the normal mechanical axis of a leg. Degenerative osteoarthritis can sometimes cause a condition in long human bones which causes the bone to change shape. Instead of being relatively straight, the bone becomes curved or misshapen over a period of time. The tibia may deviate in an outward direction (valgus), in an inward direction (varus), or compound shapes. Most frequently, the valgus or varus condition occurs at the base joint, affecting the mechanical load on the knee. The result of this condition is that the mechanical axis of the leg becomes altered, with resultant load patterns that the knee joint cannot properly accommodate. Great pain and difficulty of movement can result, with a consequent restriction of lifestyle. A further problem associated with this condition is increased joint arthritis due to improper load distribution. In younger patients, improper bone growth can lead to similar problems, and require similar treatment. Examples of this condition are commonly known as bow-leggedness (genu varum) or knock knee (genu valgum).

Among the techniques developed for dealing with valgus or vams conditions, one of the most successful is known as cuneiform or wedge osteotomy. Treatment requires that the angular deformity be determined by one of several methods. The desired correction angle is determined by adding the preoperative varus angle or valgus angle to the desired postoperative valgus angle. Generally, between five and thirteen degrees of valgus have been shown to result in the most successful outcome in osteotomy procedures.

In performing a cuneiform or wedge osteotomy, a wedge shaped section of bone is surgically removed to allow realignment of the bone. The wedge cut made by the surgeon should not completely sever the tibia, however. A bridge of residual bone should remain uncut, this portion serving in effect as a hinge for reduction of the wedge-shaped gap that remains following removal of the bone wedge. The depth of the wedge is critical in that if the wedge is too shallow, thus rendering the bridge too wide, the resulting wide fulcrum results in over stressing of the medial cortex during wedge compression, causing fracture of the bone bridge. If the wedge is too deep (the residual bone bridge is too narrow) the residual bone bridge, if not completely severed, lacks significant strength to provide medial stability to the reduced osteotomy. Reduction of the wedge-shaped gap allows realignment of the bone, and correction of the loading patterns of the leg. Bone plates will be installed to secure the reshaped bone, at least through the healing process.

Several types of devices have been developed to assist the surgeon in carrying out the osteotomy process. One type of device comprises a sequence of jigs which are affixed to the tibia in a position determined by the surgeon. This requires the drilling of holes in the tibia to anchor the jigs. A first jig contains a single slot through which the surgeon inserts the blade of an oscillating bone saw and makes a first cut. The first jig is removed and a second jig containing a series of slots corresponding to different angles is then affixed to the same position as the first jig. The surgeon inserts the oscillating bone saw blade into the desired slot and makes a second cut. The second cut should terminate at the same point as the first cut, creating a clean apex. Ideally, this allows a section of bone to remain intact. Careful compression of the resected area reshapes the bone, and it is secured by the placement of an osteotomy bone plate.

Problems in using jig-based devices include the possibility of inaccurate estimation of the resection surfaces, resulting in an insufficient area of residual bone, or even of a severing of the upper part of the tibia. Also, the two cuts may not be aligned properly, resulting in an unclean cut which could interfere with the compression and reduction process, and also affect the healing process. Prior-art jigs are usually rigid devices which are unable to adjust to the varied contours of an individual patient's anatomy. Thus, using such devices is often a compromise, and can lead to less than ideal results.

Other devices are also known which provide varying degrees of adjustability to allow the surgeon to select a predetermined desired angle. These devices typically require the surgeon to make an unaided first cut. The device includes a flat, blunt blade which is inserted into the first cut. The surgeon then adjusts the angle of the saw blade guide on the device to create a properly angled wedge to be excised from the bone. Problems with such devices include a lack of precision, with the possibility of locating the wedge apex too shallow or too deep and producing an improperly sized or angled wedge.

What is clearly needed, therefore, is a method and instrumentation for performing osteotomy procedures which allows greater accuracy and improved precision in determining the location of the resection surfaces.

SUMMARY OF THE INVENTION

An adjustable tibial osteotomy jig, comprises a goniometer, and the goniometer further comprises first and second arms, each arm having a base. A pivot movably connects the arms at their bases. The pivot has a bore passing through it. A thumb-screw and knob locking devices are provided for locking the arms of the goniometer in a predetermined angular relationship. The jig has a scale for angular measurement of the relative positions of the arms.

A proximal cutting guide is slidably mounted on the first arm, and a distal cutting guide is slidably mounted on the second arm. Each of the cutting guides has a transverse slot extending therethrough to define a cutting surface, and one or more holes extending therethrough. Each cutting guide has a clamp connected to it for locking each cutting guide in a predetermined radial position along its respective arm.

One or more pins pass through the holes in the proximal cutting guide and into a tibia, for fixing the proximal cutting guide in a first predetermined position with respect to the tibia. One or more pins pass through the holes in the distal cutting guide for fixing the distal cutting guide in a second predetermined position with respect to the tibia. The surgeon passes the blade of a saw through the slots of the cutting guides, which results in a cut removing a wedge-shaped piece of bone from the tibia, the wedge having an angle equal to the predetermined angular relationship.

DESCRIPTION OF THE DRAWINGS

FIG. 2 is a perspective, cut-away view of a cutting guide and the lock movably attaching it to a goniometer arm.

FIG. 3 is a perspective view of the cutting guide from another angle.

FIG. 4 is a perspective view of the lock.

DETAILED DESCRIPTION

Figure 1:
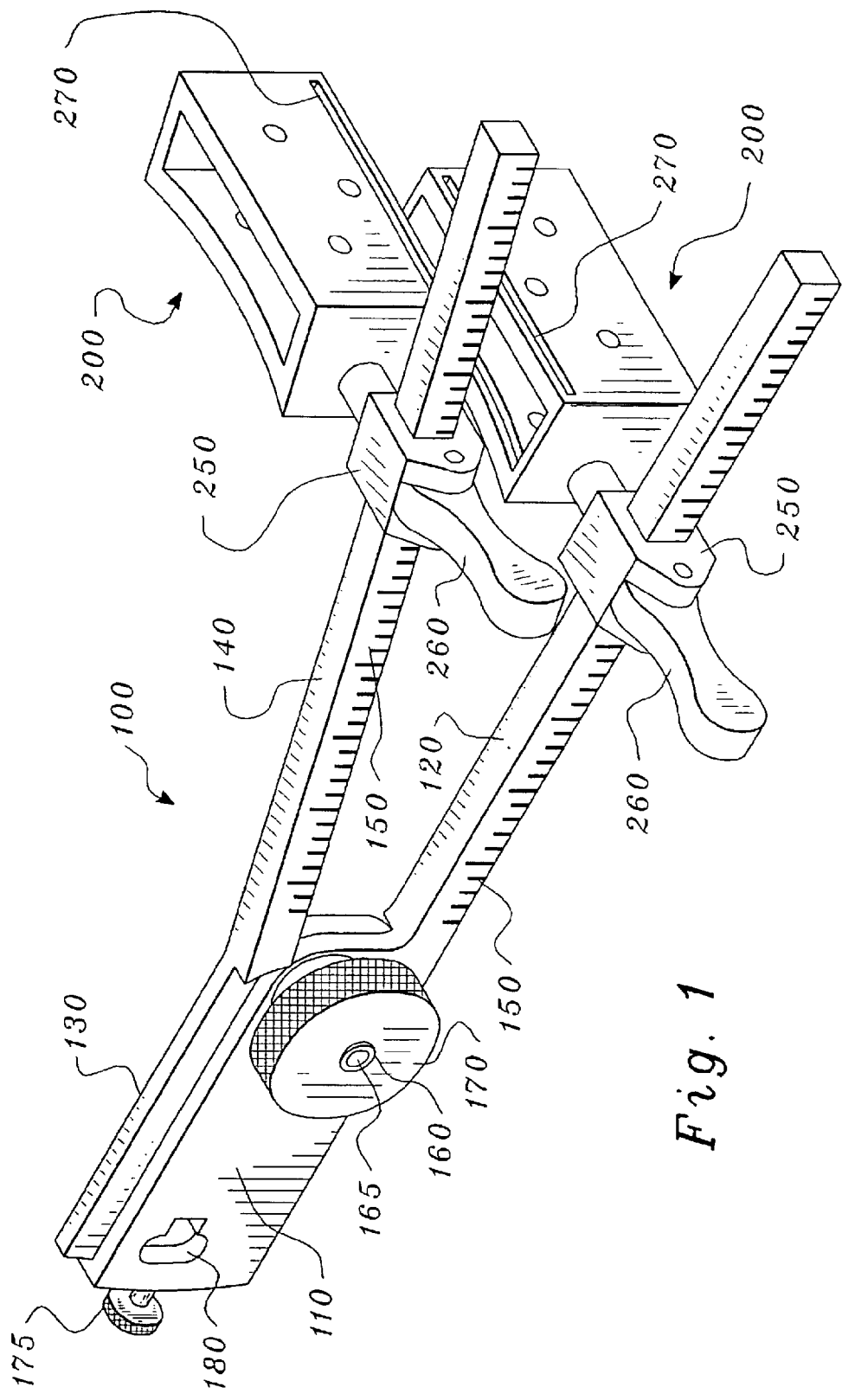
FIG. 1 is a perspective view of the goniometer.

FIG. 1 shows the goniometer (100) used to measure and set the correct angle for the bone wedge to be cut from the tibia (300). The goniometer (100) has a first arm (140) having a first base (130), and a second arm (120) having a second base (140). In the preferred embodiment, there is a scale (180) suitably graduated in angular measurement. The first base (130) and the second base (140) are rotatably mounted about a pivot (160). The pivot (160) has a bore (165) for receiving a pin, as described below. The goniometer (100) has a locking device (175), such as a thumbscrew, for holding the arms in a desired position. The pivot preferably also has another locking knob (170), for securely fixing the arms relative to one another. Each arm (140, 120) of the goniometer (100) has graduations of linear measurement (150).

FIGS. 2, 3, and 4 show the cutting guides (200) of the preferred embodiment. The cutting guide (200) has a first face (210) which is preferably curved, and a second face (220) which is preferably flat. The cutting guide (220) may be hollow as shown, to reduce weight, or it may be solid. In either case, the cutting guide (200) has a plurality of holes (230) passing through it. Each cutting guide (200) has attached a clamp (250) adapted to slidably fit over an arm (120, 140) of the goniometer (100). Each clamp (250) has a locking mechanism (260), which may be a cam lock, as shown or a spring-and-detent lock, or some other means of fixing the clamp (250) to an arm (120,140) of the goniometer (100). Each cutting guide (200) has a transverse slot (270) passing through it. This slot (270) receives and guides a saw blade.

I will now explain the procedure for using the apparatus described above. Assume the patient has medial compartment arthrosis with a varus knee. That is, the patient's knee is bent inward; he is knock-kneed. If the normal mechanical axis is 0 degrees, the correction should be +2 degrees. The normal anatomic axis is 6 degrees valgus, so the correction should be 8 degrees valgus. The desired angle of correction is calculated from the anatomic and mechanical alignment of weight-bearing AP (anterior-posterior) radiographs.

First, we perform arthroscopic debridement and any necessary biologic repair. The lateral joint line is preferably marked with two K-wires (Kirschner wires) placed under the lateral meniscus, and one K-wire placed under the medial meniscus. We then expose the anterolateral proximal tibia.

Figure 5:
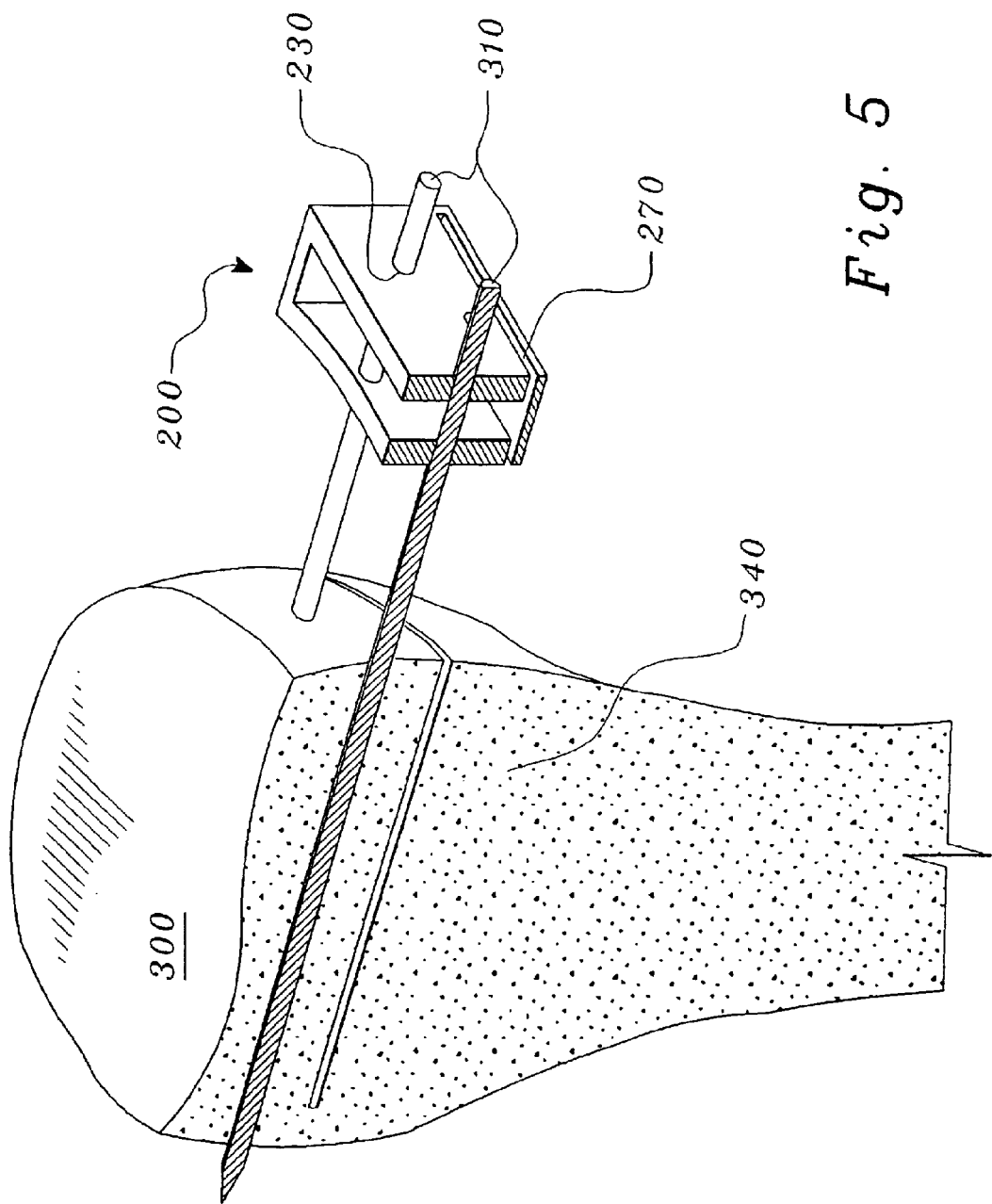
FIG. 5 is a perspective view of the proximal cutting guide of the preferred embodiment pinned to a tibia to establish the location of the transverse cut.

As shown in FIG. 5, we place the first, or proximal, cutting guide (200) approximately 2 cm below the lateral joint line. We place proximal parallel guide pins (310) through the cutting guide (200) holes (230) so that the threaded tips of the guide pins (310) engage the medial cortex of the tibia (300) when inserted through the cutting guide (200) holes (250) and through the tibia (300).

Figure 6:
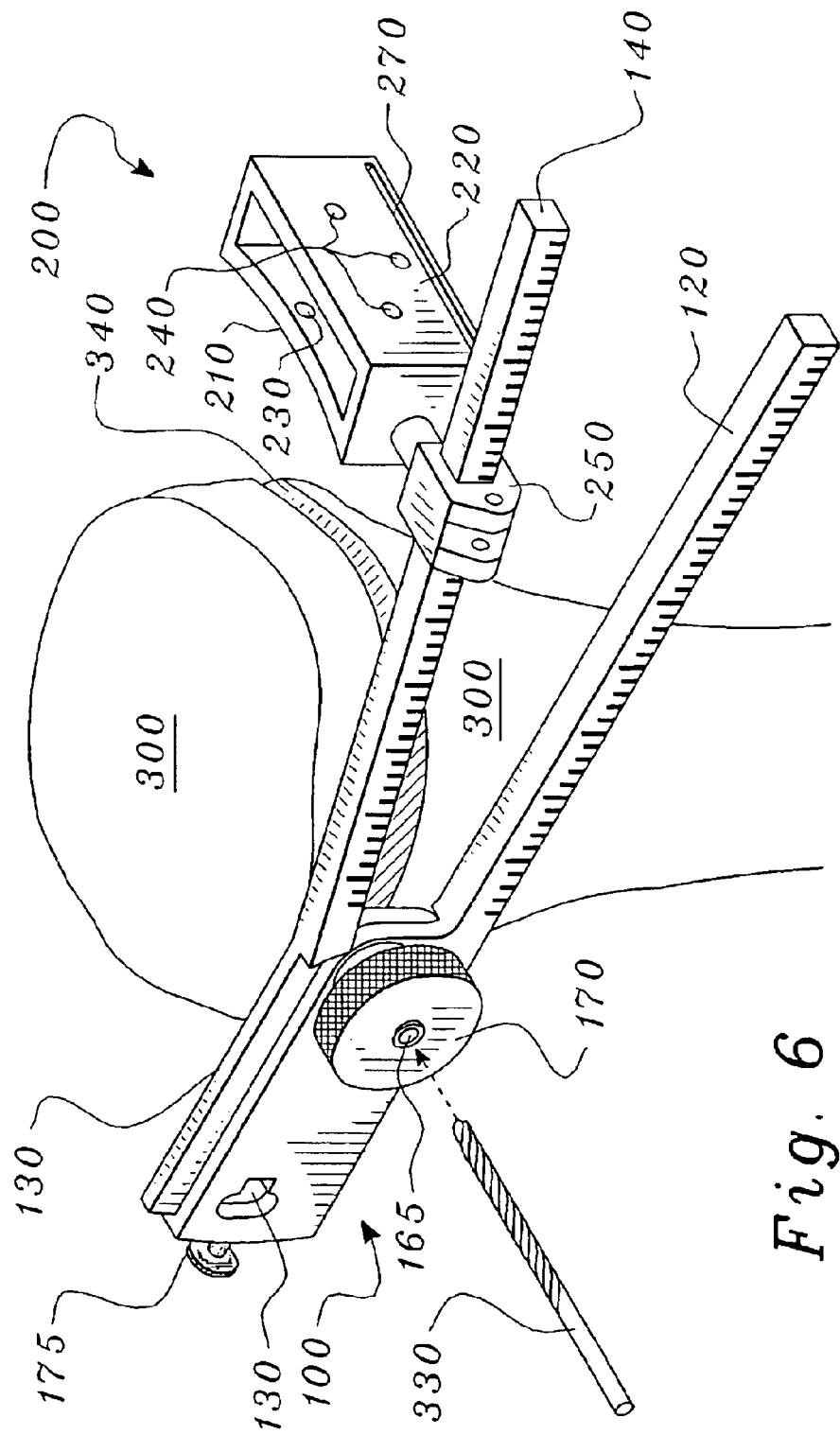
FIG. 6 is a perspective view of the preferred embodiment with the goniometer arm locked to the proximal cutting guide after the transverse cut has been made.

FIG. 6 shows how the first arm (140) of the goniometer (100) is placed through the pinned proximal cutting guide (200) and locked in place so that the pivot (160) of the goniometer (100) is located over the bone bridge. An AP pin (usually a twist drill bit) (330) is passed through the bore (165) of the pivot (160) into the bone bridge. After measuring the length of the guide pins (310), we use a calibrated saw to make the transverse osteotomy cut (240) in the tibia (300). This cut should be about 10 mm less than the length of the longest guide pin (310) to leave a bone bridge after the final cut. Using the angle scale (180) of the goniometer (100) we set the angle between the goniometer arms (120, 140) to the previously-calculated correction angle.

Figure 7:
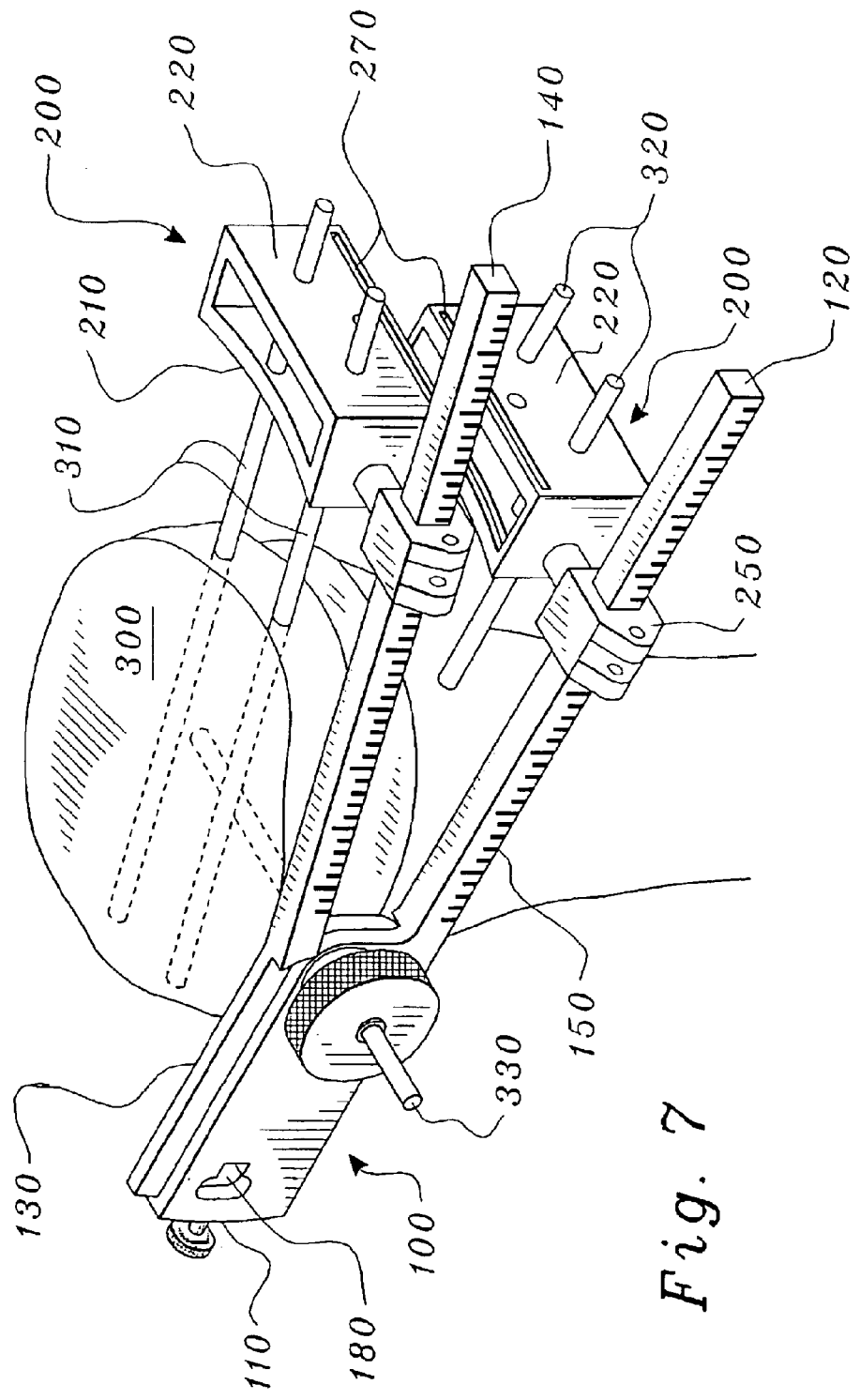
FIG. 7 is a perspective view of the preferred embodiment showing the goniometer pinned to the tibia and the distal cutting guide fixed to the second arm of the goniometer.
Figure 8:
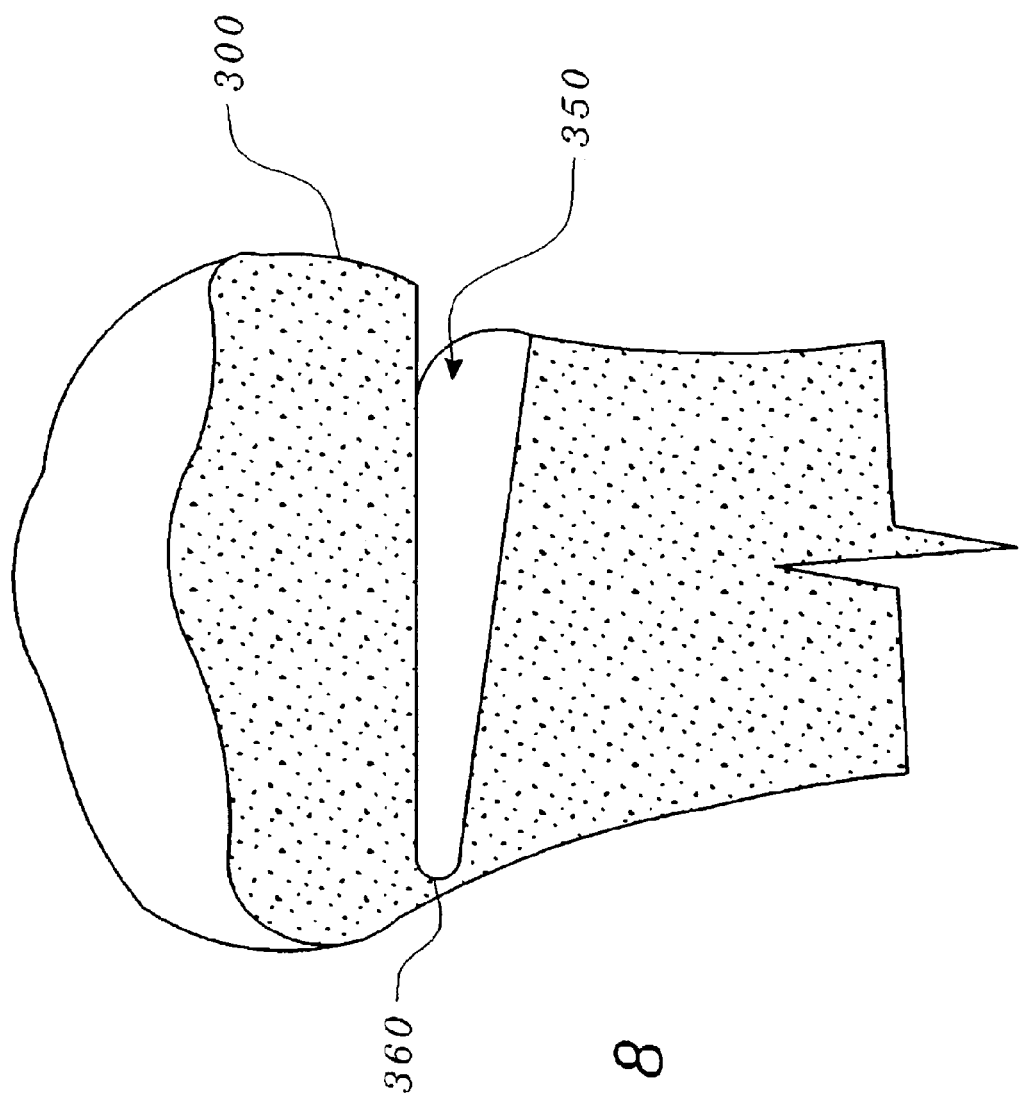
FIG. 8 is a perspective view of the tibia after the final cut has been made to define the bone wedge that is removed.

FIG. 7 shows a second, distal, cutting guide (200) slidably attached to the second arm (120) of the goniometer (100). The second cutting guide (200), as shown in FIG. 7, is pinned in place with pins (320) passing through it and obliquely into the tibia (300). The saw blade is now passed through the slot (270) of the second cutting guide (200) and the oblique cut is made to define the wedge of bone to be removed. The result is shown in FIG. 8. FIG. 8 also shows the radius (360) left at the apex of the cut (350), after drilling with the twist drill (330). This radius relieves stress at the apex of the cut and makes splitting of the bone less likely. A surgical clamp may be attached to the four (or more) pins (310, 320) and compression applied to close the wedge. The bone is fixed by conventional means, such as bone plates, and the wound closed.

Although I have described the invention in terms of specific embodiments, I anticipate that alterations and modifications of it will no doubt become apparent to those skilled in the art. I therefore intend that the following claims be interpreted as covering all such alterations and modifications as fall within the scope of the invention.

I claim:

1. An adjustable tibial osteotomy jig, comprising:
   a. a goniometer, the goniometer further comprising:
      (1) first and second arms;
      (2) a pivot movably connecting the arms;
      (3) a locking device for locking the arms in a predetermined angular relationship;
   b. a proximal cutting guide, slidably mounted on the first arm;
   c. a distal cutting guide, slidably mounted on the second arm;
   d. each of the cutting guides having a transverse slot extending therethrough to define a cutting surface, and one or more holes extending therethrough; and,
   e. a clamp connected to each cutting guide for locking each cutting guide in a predetermined radial position along its respective arm.

2. The adjustable tibial osteotomy jig of claim 1, further comprising a base attached to each arm; the pivot movably connecting the arms at the bases.

3. The adjustable tibial osteotomy jig of claim 1, where the pivot has a bore passing through it for receiving a pin.

4. The adjustable tibial osteotomy jig of claim 1, where the locking device comprises a thumbscrew and a locking knob tightening the arms together.

5. The adjustable tibial osteotomy jig of claim 1, further comprising a one or more pins; the pins passing through the holes in the proximal cutting guide and into a tibia, for fixing the proximal cutting guide in a predetermined position with respect to the tibia.

6. The adjustable tibial osteotomy jig of claim 1, further comprising a one or more pins; the pins passing through the holes in the distal cutting guide and into a tibia, for fixing the distal cutting guide in a predetermined position with respect to the tibia.

7. An adjustable tibial osteotomy jig, comprising:
  a. a goniometer, the goniometer farther comprising:
    (1) first and second arms, each arm having a base;
    (2) a pivot movably connecting the arms at their bases; the pivot having a bore therethrough;
    (3) a locking device for locking the arms of the goniometer in a pre-determined angular relationship; and,
    (4) a scale for angular measurement of the relative positions of the arms;
  b. a proximal cutting guide, slidably mounted on the first arm;
  c. a distal cutting guide, slidably mounted on the second arm;
  d. each of the cutting guides having a transverse slot extending therethrough to define a cutting surface, and one or more holes extending therethrough;
  e. a clamp connected to each cutting guide for locking each cutting guide in a predetermined radial position along its respective arm;
  f. one or more pins passing through the holes in the proximal cutting guide and into a tibia, for fixing the proximal cutting guide in a first predetermined position with respect to the tibia; and,
  g. one or more pins passing through the holes in the distal cutting guide for fixing the distal cutting guide in a second predetermined position with respect to the tibia.

8. A method of performing a tibial osteotomy, comprising the steps of:
  a. providing a an adjustable tibial osteotomy jig, the jig comprising:
    (1) a goniometer, the goniometer further comprising:
      (i) first and second arms;
      (ii) a pivot movably connecting the arms; the pivot having a bore therethrough;
      (iii) a locking device for locking the arms in a predetermined angular relationship;
    (2) a proximal cutting guide, slidably mounted on the first arm;
    (3) a distal cutting guide, slidably mounted on the second arm;
    (4) each of the cutting guides having a transverse slot extending therethrough to define a cutting surface, and one or more holes extending therethrough; and,
    (5) a clamp connected to each cutting guide for locking each cutting guide in a predetermined radial position along its respective arm;
  b. calculating a correction angle appropriate to the osteotomy and determining the lateral line for the transverse osteotomy cut;
  c. placing the proximal cutting guide against the tibia in a predetermined position below the lateral line;
  d. fixing the proximal cutting guide in the predetermined position by passing one or more guide pins through the holes in the proximal cutting guide and into the tibia;
  e. extending a saw blade through the transverse slot of the proximal cutting guide and making a transverse cut through the tibia to a distance less than the depth of the tibia;
  f. attaching the first arm of the goniometer through the clamp of the proximal cutting guide and locking the first arm into a predetermined position with the clamp;
  g. fixing the goniometer to the tibia in the predetermined position by inserting a fixation pin through the bore and into the tibia;
  h. adjusting the relative angle of the goniometer arms to the calculated correction angle by adjusting the second arm of the goniometer;
  i. locking the goniometer arms to maintain the calculated correction angle;
  j. placing the distal cutting guide onto the second arm of the goniometer by passing the clamp of the distal cutting guide over the second arm to a position near the tibia;
  k. locking the distal cutting guide onto the second arm;
  j. fixing the distal cutting guide in the predetermined position just obtained by passing one or more guide pins through the holes in the distal cutting guide and into the tibia;
  k. extending a saw blade trough the transverse slot of the distal cutting guide and making an oblique cut through the tibia to a distance less than the depth of the tibia, and meeting the reverse cut;
  l. removing a wedge-shaped portion of the tibia formed by the transverse and oblique cuts through the tibia to form a void in the tibia; the void being defined by an upper side, created by the transverse cut, and a lower side, created by the oblique cut; and,
  m. drawing the upper and lower sides of the tibia together and permanently closing the void.

* * * * *

UNITED STATES PATENT AND TRADEMARK OFFICE
CERTIFICATE OF CORRECTION

PATENT NO.     : 6,796,986 B2
DATED          : September 28, 2004
INVENTOR(S)    : David W. Duffner It is certified that error appears in the above-identified patent and that said Letters Patent is hereby corrected as shown below:

Column 5,
Line 20, the word "farther" should be -- further --.

Column 6,
Line 45, the word "trough" should be -- through --.

Signed and Sealed this

Fourth Day of January, 2005

JON W. DUDAS
*Director of the United States Patent and Trademark Office*